United States Patent [19]

Watts, Jr. et al.

[11] 4,222,957

[45] Sep. 16, 1980

[54] PROCESS OF PURIFYING ETHER SULFONATES

[75] Inventors: Lewis W. Watts, Jr.; Walter H. Brader, Jr.; Philip H. Moss; Ernest L. Yeakey, all of Austin, Tex.

[73] Assignee: Texaco Development Corp., White Plains, N.Y.

[21] Appl. No.: 963,616

[22] Filed: Nov. 24, 1978

Related U.S. Application Data

[63] Continuation-in-part of Ser. No. 791,751, Apr. 28, 1977, abandoned.

[51] Int. Cl.$^2$ ............................................. C07C 143/38
[52] U.S. Cl. .............................. 260/512 R; 260/513 R
[58] Field of Search ......................... 260/512 R, 513 R

[56] References Cited

U.S. PATENT DOCUMENTS

| | | | |
|---|---|---|---|
| 3,228,979 | 1/1966 | Gaertner | 260/512 R |
| 3,450,749 | 6/1969 | Furrow | 260/513 B |
| 4,048,221 | 9/1977 | Wolf et al. | 260/513 R |

*Primary Examiner*—Natalie Trousof
*Assistant Examiner*—Vera C. Clarke
*Attorney, Agent, or Firm*—Carl G. Ries; Robert A. Kulason; James L. Bailey

[57] ABSTRACT

Covers a method of purifying ether sulfonates by contact with ethylene oxide or propylene oxide.

5 Claims, No Drawings

PROCESS OF PURIFYING ETHER SULFONATES

REFERENCE TO RELATED APPLICATIONS

This application is a continuation-in-part application of Ser. No. 791,751, filed Apr. 28, 1977, now abandoned.

BACKGROUND OF THE INVENTION

1. Field of the Invention

The present invention relates to the purification of organic sulfonates, and particularly organic ether sulfonates.

2. Description of the Prior Art

Organic sulfonates such as organic ether sulfonates are becoming increasingly important due to their use in liquid detergents, particularly in the preparation of relatively salt-free detergents having good solubility characteristics. Even more recently, the compounds of this general type have been found to be useful materials when employed as surfactants for enhanced oil recovery processes.

In many instances the process of choice used in making ether sulfonates often results in a product having impurities present which cannot be tolerated in view of many contemplated end uses of such impure products. In many instances, the impurities take the form of various organic and inorganic ionic species. Thus, for example, anions such as sulfite and sulfate may be present which interfere somewhat in the performance of the ether sulfonate for its chosen utility. In other cases, diionic organic impurities may be present, such as disulfonates and disulfinates. In still other instances, both inorganic and organic impurities of this type or others are present.

As just one example of the above it has been determined that a chemical to be useful as an additive in promoting oil recovery must have the proper hydrophobic-hydrophilic ratio or HLB balance. Undue amounts of ionic impurities will destroy such desired balance leading to lesser activity of the active ingredient.

It would therefore be a substantial advance in the art if a method were known of purifying organic ether sulfonates by freeing them of deleterious ionic species of the organic or inorganic type such as those mentioned above or others.

It is therefore a principal object of this invention to provide a process for the purification of organic ether sulfonates whereupon said sulfonates are freed of injurious ionic impurities which tend to interfere with the ultimate performance of the ether sulfonate product.

A specific object of the invention is to provide the just mentioned purification method which can be carried out simply, and economically without resort to sophisticated equipment and multi-steps. The above-mentioned objects and advantages of the present invention will become apparent as the invention is more thoroughly set out hereinafter.

SUMMARY OF THE INVENTION

In its broadest aspect the present invention comprises a method of purifying ether sulfonates containing organic or inorganic ionic impurities, said ether sulfonates having the formula:

$$R-O+R_3)SO_3A$$

where R is a radical selected from the group consisting of $C_1-C_{30}$ alkyl, $C_1-C_{30}$ alkenyl, $C_1-C_{30}$ substituted alkyl, $C_1-C_{30}$ substituted alkenyl, alkaryl containing one or more $C_1-C_{18}$ alkyl groups substituted on said aryl group, aralkyl containing 7-28 carbon atoms, and polyether derivatives of any of the foregoing, $R_3$ is a straight chain alkylene or alkyl substituted alkylene radical and A is an alkali or alkaline earth metal cation, which comprises the step of contacting said ether sulfonate containing said impurities with ethylene oxide or propylene oxide and thereafter separating out a purified ether sulfonate.

DESCRIPTION OF THE PREFERRED EMBODIMENTS

In more detail the ether sulfonates broadly described above which are subjected to the purification techniques discussed here are known materials and need not be discussed in any detail here. Moreover, their mode of preparation may be selected from a number of disclosed techniques. Neither the class of ether sulfonates described here nor their method of preparation forms any part of this invention.

Likewise, the ionic impurities which may be present and which are removed from the ether sulfonates by the procedure here may be of diverse character. The amount of impurities present and their particular ionic form will largely depend upon the process chosen for preparing the ether sulfonate materials to be purified. In any event, it has been found here that the techniques of purification are applicable to separating out both inorganic and organic monoionic and polyionic charged compositions. Thus, for example, such impurities may be in the form of anions such as sulfate, sulfite, bisulfate, bisulfite, and the like. In like manner the impurities may be in the form of diionic organic sulfonates and sulfinates. The invention is particularly applicable to removal of such organic diionic compounds and sulfite or bisulfite ions.

In one particular scheme of preparing the above defined ether sulfonates organic diionic compounds and bisulfite remain as an impurity. This method disclosed in copending, commonly assigned application Serial No. 775,657 filed Mar. 3, 1977 involves the steps of reacting an alkoxylated alcohol having the formula:

$$R+O-CH_2-CH)_{\overline{z}}OH$$
$$\phantom{R+O-CH_2-CH}|$$
$$\phantom{R+O-CH_2-CH}R_1$$

where R is as above, $R_1$ is H or $CH_3$ and z is an integer of 1–40 with an alkyl halide having the formula:

$$XCH_2CR_1=CH_2$$

where X is halo and $R_1$ is H or $CH_3$ in presence of a base to produce an allyl ether having the formula:

$$R+O-CH_2-CH)_{\overline{z}}O-CH_2-CR_1=CH_2$$
$$\phantom{R+O-CH_2-CH}|$$
$$\phantom{R+O-CH_2-CH}R_1$$

where R, $R_1$ and z are as above and reacting said allyl ether with an alkali metal bisulfite such as sodium or potassium bisulfite to produce an ether sulfonate of the formula:

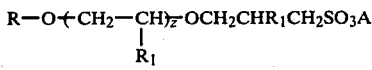

where A is an alkali metal or alkaline earth metal cation.

The ether sulfonate containing impurities is purified via contact with ethylene oxide or propylene oxide in any manner involving the proper intimate contact. For example, such purification contact may be carried out by means of an autoclave. Again, the purification itself may be effected over a wide range of process variables of time, temperature, pressure, etc. Usually, the purification is carried out at a temperature ranging from about room temperature up to about 250° C. More often the temperature of purification is 25°–200° C. and most often ranges from about 50° to about 150° C. The time of contact likewise may be considerably varied from about ¼ to about 24 hours. More often the purification step is complete in 1–10 hours. Again, while the purification may be run at atmospheric pressure, usually it is more usefully carried out at super atmospheric pressures or autogenous pressures. Usually the pressure ranges from about 5 to about 500 psig. More often the pressure is 5–100 psig.

Again, the amount of ethylene oxide or propylene oxide purification reagent or mixture of the two used may be widely varied. Usually a slight excess of reagent is present, calculated upon the amount of impurities present, which amount may be determined by known analytical techniques. For example, if bisulfite is present it may be determined by such known procedures as titration. Again, if diionic organics are present high pressure liquid chromotography may be used. After determination of the amount of impurities present the ethylene oxide or propylene oxide may be added in equal molar amounts or in excess. As one example 8–10 percent excess of oxide is employed. Usually if a diionic organic species is present it is sufficient to react it with only enough ethylene oxide or propylene oxide to convert the impurity to a mono-ionic species. Thus, only one half mole per mole of diionic impurity present need be added of the oxide reagent. On the other hand, if an impurity is present such as sodium bisulfite usually at least one mole of ethylene or propylene oxide or mixtures of the two are added per mole of sodium bisulfite present as an impurity.

One particularly useful technique found here involves carrying out the purification while the ether sulfonate is dissolved in an aqueous medium. This medium may be water itself, but is preferably a mixture of water and a water miscible organic solvent such as a lower alkyl alcohol, preferably, one containing 1–4 carbon atoms. Typical reagents of this type include isopropyl alcohol.

When a water-alcohol solution of ether sulfonate is treated with ethylene oxide, propylene oxide or a mixture of these oxides it has been found that two distinct layers are formed. The bottom layer has been found to contain substantially all of the former impurities in some modified chemical form, whereas the top layer contains the purified ether sulfonate or active ingredient. The two layers are then simply separated one from the other to provide a surprisingly pure ether sulfonate solution.

Greatly preferred ether sulfonates which may be purified here fall within the following structural formula:

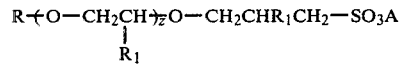

where R is a radical selected from the group consisting of $C_1$–$C_{30}$ alkyl, $C_1$–$C_{30}$ alkenyl, $C_1C_{30}$ substituted alkyl, $C_1$–$C_{30}$ substituted alkenyl, alkaryl containing one or more $C_1$–$C_{18}$ alkyl groups substituted on said aryl group and aralkyl containing 7–28 carbon atoms, $R_1$ is H or $CH_3$, z is an integer of 1–40, and A is an alkali or alkaline earth metal cation.

The following examples specifically illustrate the purification process of the invention. It should be understood, of course, that these examples are merely illustrative and that the invention is not be limited thereto.

EXAMPLE I

A mixture of an allylated-nonylphenol ethoxylate (4 mole adduct) (75 gms), $NaHSO_3$ (35.4 gms), $KNO_3$ (2 gms), $H_2O$ (150 ml), and t-butanol (150 ml) was charged to a clean, dry, air purged clave. The resulting material

derived from heating said mixture at 100° C. and 20 psig air for 1 hour followed by holding at 120° C. and 50 psig air for 1 hour was a homogeneous solution. Analysis indicated the presence of strong acid (1.06 meq/gm) and 0.02% Cl.

EXAMPLE II

To 327 gms of the crude product described in Example 1 contained in a 1 1 stirred autoclave there was added 12 gms of ethylene oxide over a period of 1 hour at approximately 110° C. Following a 1½ hour digestion period at 110° C. and cooling to room temperature the contents of the clave were transferred to a separatory funnel, whereupon two layers were isolated. The lower layer (73.5 gms) proved to contain 2.0 meq/gms strong acid and 1.4% of the active ingredient, i.e., the desired sulfonate salt, basis analytical data. Importantly, the upper layer was a pale yellow liquid containing only 0.5 meq/gm strong acid and almost 99% of the desired sulfonate salt.

EXAMPLE III

In the same manner as described in Example 1, the allyl compound (75 gms), $NaHSO_3$ (35.4 gms), $KNO_3$ (2 gms), t-butanol (150 ml), and $H_2O$ (150 ml) were heated at 100° C. in the presence of air (30 psig) for 1 hour, then at 120° C. for 1 hour (50 psig air). Analysis of the resulting homogeneous mixture indicated the presence of 0.955 meq/gm strong acid and 0.32 meq/gm sulfonate salt.

EXAMPLE IV

As per Example II, the product formed in Example III (315 gms crude reaction mixture) was treated with propylene oxide (15 gms) at 110° C. for approximately 2 hours. Analysis of the crude two phase mixture indicated most of the strong (undesired) acid was concentrated in the lower phase (47 gms in layer, 1.90 meq/gms). Most importantly the upper phase contained greater than 99% of the desired active ingredient ether sulfonate in an amount of 256 gms straw colored liquid.

EXAMPLE V

The allyl ether of the 3-mol ethylene oxide adduct of dodecylphenol was sulfonated by the following procedure:

A mixture of 160 g allyl ether of the 3-mol ethylene oxide adduct of dodecylphenol (342 meq), 160 g isopropyl alcohol, 350 g water, 6.3 g sodium sulfite (50 meq) and 30 g of a 25% solution of product sulfonate from a previous preparation (14 meq) acting as an emulsifier was heated to 55° and neutralized to pH 7.2 by a 33.5% aqueous solution of sodium metabisulfite. Air was bubbled into the mixture at a rate of 8 ml/min. Metabisulfite solution was added over 7 hours at a rate to maintain constant pH.

Analysis by iodometry of the product revealed a total sulfite level of 0.068 meq/g.

The reaction as just described was then repeated. At its completion 2 ml ethylene oxide were added; the pH rose to 9.12. After alcohol solvent removal by distillation the sulfite level was reduced to 0.027 meq/g.

EXAMPLE VI

The allyl ether of the 4-mol ethylene oxide adduct of n-octanol was sulfonated by the procedure described in Example V. At the end of the reaction the sulfite concentration was 0.410 meq/g, and the pH was 7.2. To 870 g of the product was added 6 g propylene oxide and digested at 60° overnight. The pH rose to 12.9, and the sulfite level dropped to 0.149 meq/g.

We claim:

1. A method of purifying aqueous solutions of ether sulfonates which contain at least bisulfite impurity, said ether sulfonates having the following structural formula:

$$R\text{-}(O\text{-}CH_2CH)_{\overline{z}}O\text{-}CH_2CHR_1CH_2\text{-}SO_3A$$
$$\vert$$
$$R_1$$

where R is a radical selected from the group consisting of $C_1-C_{30}$ alkyl, $C_2-C_{30}$ alkenyl, $C_1-C_{30}$ substituted alkyl, $C_2-C_{30}$ substituted alkenyl, alkaryl containing one or more $C_1-C_{18}$ alkyl groups substituted on said aryl group and aralkyl containing 7-28 carbon atoms, $R_1$ is H or $CH_3$, z is an integer of 1-40 and A is an alkali metal cation, which comprises the steps of contacting said aqueous solution with ethylene oxide or propylene oxide at a temperature ranging from about room temperature up to about 250° C. for a time ranging from about ¼ to about 24 hours and separating out a resultant top aqueous layer of purified ether sulfonate from a bottom aqueous layer containing said impurity.

2. The method of claim 1 wherein said aqueous solution is a mixture of water and alcohol.

3. The method of claim 2 wherein said alcohol is a lower alkyl alcohol.

4. The method of claim 3 wherein said lower alkyl alcohol is isopropyl alcohol.

5. The method of claim 1 wherein $R_1$ is H.

* * * * *